(12) United States Patent
Frischke et al.

(10) Patent No.: US 12,239,832 B2
(45) Date of Patent: Mar. 4, 2025

(54) MANNER OF RAISING ALARM FOR A HEART SUPPORT SYSTEM

(71) Applicant: Berlin Heart GmbH, Berlin (DE)

(72) Inventors: Michael Frischke, Rangsdorf (DE); Florian Jankowsky, Friedland (DE)

(73) Assignee: Berlin Heart GmbH, Berlin (DE)

( * ) Notice: Subject to any disclaimer, the term of this patent is extended or adjusted under 35 U.S.C. 154(b) by 396 days.

(21) Appl. No.: 17/769,867

(22) PCT Filed: Oct. 9, 2020

(86) PCT No.: PCT/EP2020/078506
§ 371 (c)(1),
(2) Date: Apr. 18, 2022

(87) PCT Pub. No.: WO2021/078544
PCT Pub. Date: Apr. 29, 2021

(65) Prior Publication Data
US 2022/0387779 A1 Dec. 8, 2022

(30) Foreign Application Priority Data
Oct. 21, 2019 (EP) .................................... 19204274

(51) Int. Cl.
*G08B 21/00* (2006.01)
*A61M 60/122* (2021.01)
*A61M 60/508* (2021.01)

(52) U.S. Cl.
CPC ........ *A61M 60/508* (2021.01); *A61M 60/122* (2021.01); *A61M 2205/18* (2013.01)

(58) Field of Classification Search
CPC .............. A61M 60/508; A61M 60/122; A61M 2205/18; A61M 60/178; A61M 60/216;
(Continued)

(56) References Cited

U.S. PATENT DOCUMENTS

| | | |
|---|---|---|
| 4,522,213 A | 6/1985 | Wallroth et al. |
| 5,652,566 A | 7/1997 | Lambert |

(Continued)

FOREIGN PATENT DOCUMENTS

| | | |
|---|---|---|
| CN | 107206161 A | 9/2017 |
| CN | 108430559 A | 8/2018 |

(Continued)

OTHER PUBLICATIONS

International Search Report of the International Searching Authority with English translation, dated Dec. 23, 2022, pp. 1-4, issued in International Application No. PCT/EP2020/078506, European Patent Office, Rijswijk, The Netherlands.

(Continued)

*Primary Examiner* — Toan N Pham
(74) *Attorney, Agent, or Firm* — Crowell & Moring LLP

(57) ABSTRACT

A heart support system is provided includes a control unit and sound-generating devices, said control unit configured to detect and process alarm events and to carry out control tasks in the heart support system. The heart support system further includes a storage device configured to store one or more defined alarm signal time curves and one or more alarm priorities. Each alarm signal time curve and each alarm priority is assigned to an alarm event. A sound-generation controller is configured such that when an alarm event is detected, the controller overlays a volume time curve onto the alarm signal time curve assigned to the alarm event in the storage device, said volume time curve based on the alarm priority assigned to the respective alarm event in the storage device and the length of time since the detection of the alarm event.

12 Claims, 7 Drawing Sheets

(58) Field of Classification Search
CPC .............. A61M 60/515; A61M 60/523; A61M 60/531; A61M 60/538; A61M 60/592; A61B 5/746; A61B 5/7405
See application file for complete search history.

(56) References Cited

U.S. PATENT DOCUMENTS

| | | | |
|---|---|---|---|
| 6,609,023 | B1 | 8/2003 | Fischell et al. |
| 7,215,991 | B2 * | 5/2007 | Besson ................ A61B 5/6838 600/509 |
| 2014/0111335 | A1 | 4/2014 | Kleiss et al. |
| 2019/0015040 | A1 * | 1/2019 | Voskoboynikov .. A61M 60/178 |
| 2019/0015571 | A1 * | 1/2019 | Voskoboynikov .. A61M 60/148 |
| 2022/0032035 | A1 * | 2/2022 | Kadrolkar ........... A61M 60/422 |

FOREIGN PATENT DOCUMENTS

| | | |
|---|---|---|
| DE | 3302321 A1 | 5/1984 |
| GB | 2130776 A | 6/1984 |
| WO | WO 2017/079798 A1 | 5/2017 |

OTHER PUBLICATIONS

First Office Action and Search Report issued by the China Intellectual Property Office for China Application No. CN 2020800731176 dated Jul. 31, 2024 (with English translation) (16 pp.).

* cited by examiner

MANNER OF RAISING ALARM FOR A HEART SUPPORT SYSTEM

CROSS-REFERENCE TO RELATED APPLICATIONS

This application is a 371 nationalization of international patent application PCT/EP2020/078506 filed Oct. 9, 2020, which claims priority under 35 USC § 119 to European patent application EP 19 204 274.5 filed Oct. 21, 2019. The entire contents of each of the above-identified applications are hereby incorporated by reference.

TECHNICAL FIELD

The patent application relates to an alarm device in heart support systems, in particular in heart support systems having a pump system connected to the circulatory system for maintaining blood circulation.

DETAILED DESCRIPTION

Figure 1:
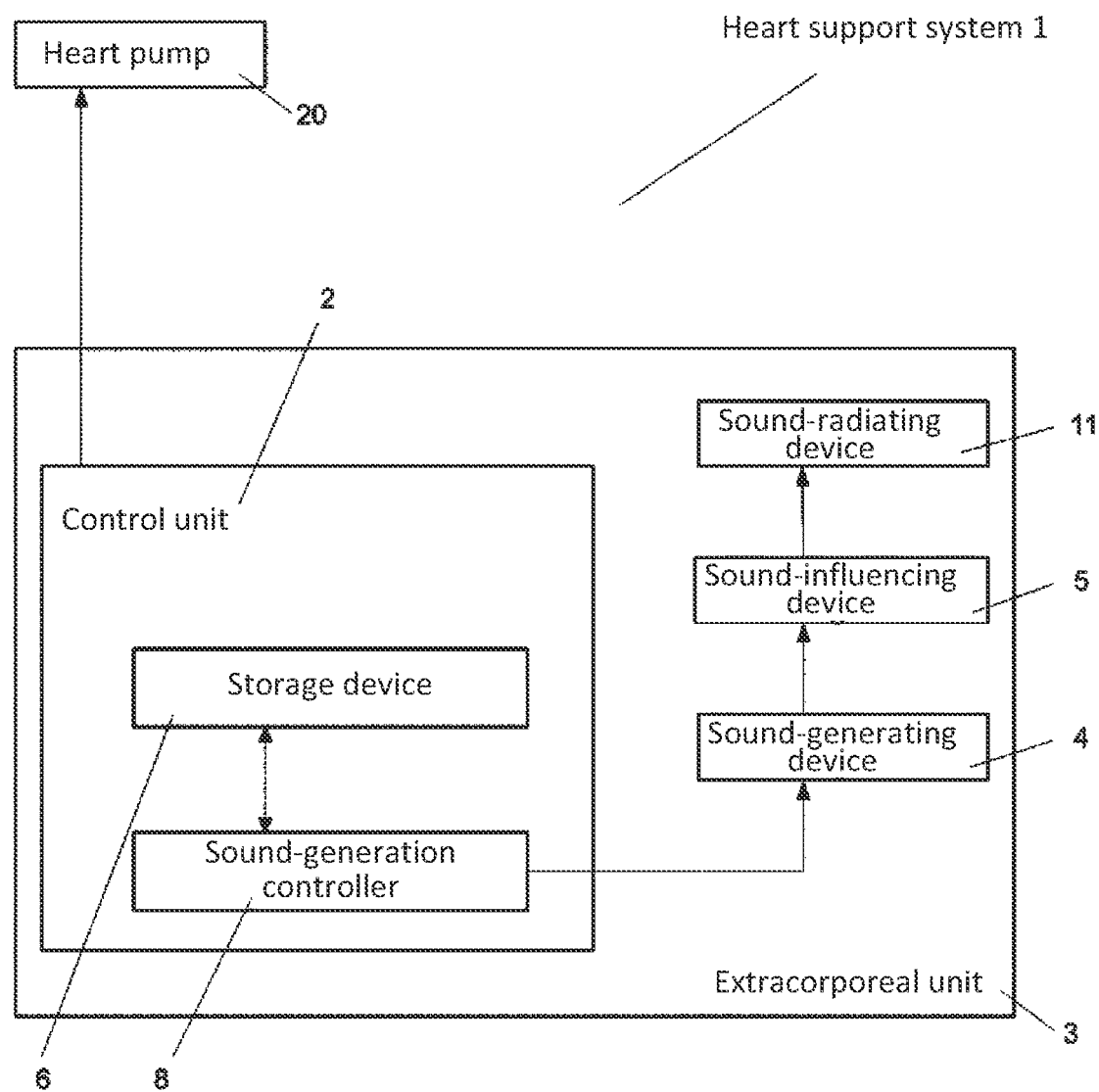
FIG. 1 illustrates a system overview of the basic alarm-relevant components of the claimed heart support system.

The output of information about the condition of the patient, but also about the device, to the medical staff or medical monitoring systems is of great importance in heart support systems. Acoustic signals are particularly important here, as they can be perceived without direct eye contact and also from a greater distance.

A possible acoustic alarm device for heart pumps is presented in patent specification EP1812094B1. The pump control system described herein comprises, among other things, a device for receiving and outputting audio signals.

The object of the claimed heart support system is to improve the existing solutions for heart support systems. In particular, the object is achieved by overlaying the time curve of the respective alarm signal by a volume time curve, which, in addition to the length of time since the arrival of an alarm event, also is based on the alarm priority assigned to the alarm event.

The term "event" means the occurrence of a certain state. The occurrence of a state is generally determined with the aid of a comparison against a reference value. The result of the comparison describes the determined state and thus the event. Depending on the context, reference values can be fixed in time or variable over time. The event has arrived in the heart support system or the event has been detected by the heart support system with the determination of the comparison result. Events are often given defined identifiers, for example, characterizing clear names or also numbers, in order to be able to process said events within the heart support system, for example, using a software program. In principle, however, processing by an electronic circuit is also possible.

States in the heart support system are defined, for example, as signed values of electrical voltages or electrical currents that can be measured between or at defined points. The comparison of the measured voltages and currents with reference values means that the occurrence of a particular state can be determined. The electrical voltages or electrical currents can be generated by sensors, for example, the generated voltages or currents being able to correspond to physical quantities such as pressure, strain, flow, length, light, sound, acceleration, magnetic field or chemical compositions of substances. However, electrical voltages or currents can also be generated directly by biological processes and derived with the aid of electrodes and fed to the heart support system at electrical inputs. Examples of this are electrocardiogram signals, electroencephalogram signals or also electromyogram signals. The amplitudes of the sensor voltages or currents are often first increased by means of an amplifier before they are applied to the heart support system and processed.

In addition to sensory and biological event sources, the heart support system itself can be a source of events and generate events by internal electronic components or the control unit of the heart support system, for example, by means of electrical voltages arising at the output of a timer, a counter, a clock or an oscillator or also voltages that are generated by heart support system components to indicate a respective internal condition. In addition, software components can also generate events in which, for example, calculation results or results of logical operations are viewed as a condition, the arrival of which is determined by comparison with a reference value.

Events are generally defined in the heart support system, so that a defined reaction of the heart support system can take place in response to a defined event. Alarm events are special events for which, among other things, a defined alarm is to be triggered as a reaction to their arrival in the heart support system. Alarm events can affect the patient and his or her condition, but also technical events such as the failure of a control unit or an electrical voltage source.

Examples of events that trigger alarms are, among other things, the failure of a critical component of the heart support system, a drop in blood flow, the removal of a plurality of power sources, or critical sensor readings that deviate significantly from their normal values. Examples of events that do not trigger alarms are, among other things, the completion of charging of an internal accumulator, the operation of the display or a button by a user, changes in sensor values within tolerance or alarm limits—for example, the change of the motor current on a small scale. Further examples of events that do not trigger an alarm include, among other things, the occurrence of defined non-critical physiological conditions that are only stored in a logbook and are later to be read out and checked by a doctor, and changes in the operating mode of the heart support system.

The claimed heart support system contains a first control unit and at least one first sound-generating device. The control unit is configured to detect and process events and in particular alarm events, and to process data and carry out control tasks in the heart support system. A control unit can be a microcontroller, a microprocessor, but also an electronic circuit that contains a plurality of components and is configured to take on control tasks.

The heart support system also contains a storage device and a sound-generation controller. The storage device can be RAM assemblies (RAM: random access memory) or ROM modules (ROM: read-only memory). In addition, other forms of memory such as EPROM (erasable programmable read only memory), EEPROM (electrically erasable programmable read only memory), FPGA (field programmable gate array) or even magnetic or solid-state hard drives are conceivable as memory. The storage device is configured to store one or more defined alarm signal time curves and one or more alarm priorities such that each alarm signal time curve and each alarm priority is assigned to one or more defined alarm events. The assignment can be implemented, for example, via a table stored in the storage, in which an alarm event and the assigned alarm priority and a pointer to a storage area which contains the alarm signal time curve assigned to the alarm event are entered in each line. As an alternative thereto, the assignment can also be implemented via a database stored in the storage. These two implementation options only represent examples and by no means a complete enumeration of possible implementation forms.

For example, an alarm signal time curve can be stored as a sequence of weighted frequencies or weighted frequency combinations. This can be done, for example, with a sequence of compilations, each compilation containing a length of time, a frequency list and a list with the volume of the frequencies contained in the frequency list. Alternatively, for example, the alarm signal time curve can be stored in the form of a sampled time curve. In principle, further options for storing the time curve of alarm signals are conceivable, so that the options given should only be understood as examples.

An alarm priority reflects the importance of an alarm event. This importance is specified with an element of a finite set, this finite set often containing only a few defined elements. Examples of such sets are M={high priority; medium priority; low priority} or also M={1; 2; 3; 4}.

Examples of important alarm events in heart support systems, that is, high-priority alarm events, are, among other things, the failure of a critical component of the heart support system, a drop in blood flow, the removal of a plurality of voltage sources, or the significant deviation of critical sensor values from their normal values. Examples of less important alarm events in heart support systems, that is, alarm events of medium or low priority, are, for example, a low charge status of a battery, the disconnection of a voltage source, the failure of a noncritical component of the heart support system or non-critical sensor values deviating from their normal values.

The sound-generation controller can be part of the control of the heart support system. For example, said sound-generation controller can be implemented as a process or function module in the software of the control and also have access to the electrical connections of the control. As an alternative to this, there is also the possibility of implementing the sound-generation controller as a hardware module within the control of the heart support system, as an independent electronic circuit or with a separate microcontroller. The sound-generation controller receives, for example, from the control of the heart support system, the information about the arrival of an alarm event and what the alarm event is.

When an alarm event occurs, the sound-generation controller of the heart support system is configured to overlay a defined volume time curve on the alarm signal time curve assigned to the alarm event in the storage device, said volume time curve being based on the alarm priority assigned to the respective alarm event in the storage device and the length of time from the arrival of the alarm event. For this purpose, the sound-generation controller retrieves the alarm priority of the event that has occurred and the alarm signal time curve from the storage device in order to subsequently modify the volume time curve of the alarm signal in a defined manner. For example, the modification is such that the volume of the alarm signal time curve is changed in a defined on-off pattern based on the alarm priority. On-off pattern means that the volume of the signal repeatedly changes from the value stored in storage to zero and vice versa in a defined manner. The time period in which the volume value is zero is referred to as the off phase, the other time periods as the on phase. The volume of the alarm signal is also increased during the on phases with increasing time up to a maximum value.

The sound-generation controller is also configured to actuate one or more sound-generating devices when an alarm event occurs such that the sound-generating devices convert the aforementioned alarm signal time curves with the aforementioned overlaid volume time curve into sound signals.

For this purpose, the sound-generating device can, for example, contain a digital-to-analog converter unit, an amplifier and a sound transducer, for example, a broadband loudspeaker, as is known from hi-fi technology or telephone applications for generating speech sound, or also a narrowband loudspeaker, such as a piezo buzzer. Broadband loudspeakers are characterized by a frequency response that can emit sound signals in large parts of the human hearing range. Narrow-band loudspeakers, on the other hand, are characterized by a characteristic frequency with which they can radiate sound; other sound frequencies, on the other hand, can only be radiated with low power. If a plurality of different sound frequencies are to be radiated using narrowband loudspeakers, a plurality of narrowband loudspeakers having different characteristic frequencies can be combined, each frequency or each narrowband loudspeaker being actuated separately from other frequencies or narrowband loudspeakers.

The digital-to-analog converter is actuated by the sound-generation controller such that the sound-generation controller sends the sampled alarm signal, the volume of which has been modified, as an input signal to the digital-to-analog converter and the digital-to-analog converter is actuated such that said digital-to-analog converter converts the received signal into a voltage signal that corresponds to the input signal and which is then amplified and forwarded to the downstream sound transducer.

Alternatively, the sound-generating device can also be implemented by means of a electronic oscillator circuit or a combination of a plurality of electronic oscillator circuits, each oscillator generating a voltage signal having a fixed frequency. The sound-generation controller controls the oscillators such that the frequencies specified in the alarm signal time curve are generated and, in a further stage, are combined additively according to the volume values specified in the alarm signal time curve and modified according to the alarm priority and length of time. In order to achieve a target volume level, the generated alarm signal can optionally be further amplified before it is passed on to one or more sound transducers.

The heart support system optionally comprises a heart pump and a control unit that controls the heart support system including the heart pump.

A further, optional feature of the claimed heart support system, which increases the fail-safety of the overall system, is at least one second, electrically operated sound-generating device that can be actuated separately from the first sound-generating device. All of the sound-generating devices together can contain at least one broadband loudspeaker and at least one narrowband loudspeaker. Optionally, however, exclusively broadband loudspeakers or exclusively narrowband loudspeakers are also possible.

The claimed heart support system can optionally contain at least one second sound-generation controller, which is configured to detect a functional failure of the first sound-generation controller and to control at least one sound-generating device such that the sound-generating device generates defined sound signals. One way of detecting the functional failure of the first sound-generation controller is for the first sound-generation controller to generate a pulsed voltage signal having a defined pattern at an electrical output during normal operation, which pulsed voltage signal is evaluated by the second sound-generation controller at an electrical input. Said evaluation can be carried out, for example, by a simple microcontroller or else by an electronic circuit. The second sound-generation controller can be configured such that said second sound-generation controller detects a deviation from the defined pattern, for example, the absence of a pulse, and then outputs a control signal that actuates the electrical control of a loudspeaker. The aforementioned electrical control of a loudspeaker can be implemented by an electronic oscillator circuit, with which a pulsed electrical voltage signal is generated which, as soon as said voltage signal is passed through to a loudspeaker, leads to the generation of a corresponding sound signal.

The heart support system can optionally contain a second electrical voltage source, which is configured to supply at least one sound-generating device and the second sound-generation controller with electrical voltage if the first electrical voltage source fails. This safety device is configured to detect the failure of the main power supply while allowing the heart support system to audibly report this error condition. For example, this optional functionality is possible using a simple diode circuit or using integrated circuits.

An optional element of the claimed heart support system is a sound-radiating device, which is configured to influence sound radiation. Said sound-radiating device can be, for example, a field of perforations or an arrangement that consists of a plurality of slot-shaped openings arranged in parallel. For fields of perforations, the opening diameters are no smaller than 2 mm and for slot structures, the slot widths are no smaller than 1.5 mm. In addition, the angle γ between the main direction of the sound radiation by the sound-radiating device and the normal vector of the display pointing away from the display is optionally less than or equal to 90°. Since the display generally points away from the wearer of the heart support system, the sound is therefore also substantially radiated away from the wearer.

Furthermore, the sound signal can optionally be influenced by a sound-influencing device which contains further elements, for example, resonance chambers or covers, films or fleece in the sound propagation path. The weighting of the sound frequencies is influenced in this way.

In addition, the claimed heart support system optionally contains a wireless interface, which is configured to exchange data with the wireless interface of an external unit. The external unit optionally has an optical signaling unit. Optionally, the external unit can also contain an acoustic signaling unit. The wireless interface can be, for example, a WLAN interface, Bluetooth interface, short-range radio interface or else a cellular radio interface, for example, for the standards GSM, GPRS, EDGE, CDMA, UMTS, HSDPA, HSPA, LTE or 5G.

The first step in the claimed method for raising alarm is the detection of an alarm event by the heart support system. The detection can be implemented both by a software program and by an electronic circuit. In this case, for example, a voltage or current value present at the system inputs is compared with a reference value or, alternatively, a calculated value or a value determined by logical operation is compared with a reference value. The type of alarm event is determined based on the type of comparison performed.

In a second method step, the alarm priority assigned to the alarm event and the alarm signal time curve assigned to the alarm event are retrieved from a storage device.

In a third method step, a defined volume time curve is overlaid on the retrieved alarm signal time curve, based on the alarm priority and on the length of time since the arrival of the alarm event. This alarm timing is modified, for example, by changing the volume of the alarm timing in a defined on-off pattern based on the alarm priority. On-off pattern means that the volume of the signal repeatedly changes from the value stored in storage to zero and vice versa in a defined manner. The time periods in which the volume value is zero are each referred to as the off phase, the other time periods as the on phase. In addition, the volume of the alarm signal is modified such that the volume during the on phases increases with increasing time measured from the detection of the alarm event up to a maximum value.

In a fourth method step, the sound-generating device is actuated such that the alarm signal time curve is converted with the overlaid volume time curve into a sound signal.

Exemplary embodiments are explained below with reference to figures.

The basic alarm-relevant components of the heart support system 1 are depicted in a system overview in FIG. 1. In this case, the heart pump 20 is arranged, for example, in a patient's body, while the other elements depicted are combined in an extracorporeal unit 3. For example, all elements of the extracorporeal unit can be located outside the patient's body in a housing. The central element of the heart support system 1 is the control unit 2. The control unit 2 is configured to detect and process events and in particular alarm events 43 and to process data and to carry out and coordinate control tasks in the heart support system. Said control unit's control tasks include, among other things, the control of the heart pump 20. A control unit 2 can be a microcontroller, a microprocessor, but also an electronic circuit which contains a plurality of components and which is configured to take on control tasks. The sound-generation controller 8 can be implemented as part of the control unit, for example, on its own processor core or else as a software process or function module within the software. In principle, however, a separate implementation in a microcontroller configured for this purpose is also possible.

An electronic storage device 6 is connected to the sound-generation controller 8, said electronic storage device storing alarm signal time curves and alarm priorities and their assignment to alarm events.

The sound-generating device 4 is controlled by the sound-generation controller 8. Said sound-generation controller comprises, for example, a digital-to-analog converter, an amplifier and a loudspeaker. The frequency composition of the sound generated by the sound-generating device is influenced by the sound-influencing device 4. The sound-influencing device 4 includes covers, films or also resonance chambers, which exert an influence on the sound signal. In addition to the sound-influencing function, films and covers can also have a protective function, for example, to protect the heart support system from moisture or particles. If the specific type of influence of the sound-influencing function is known, it can be taken into account by the sound-generating device 4 in the course of sound signal generation, for example, by additional digital or analog filtering or by adapting the alarm time curve stored in the storage device.

The sound-radiating device 11 comprises components which influence the sound radiation, for example, horn geometries, fields of perforations or slot structures. For fields of perforations, the opening diameters should be no smaller than 2 mm and for slot structures, the slot widths should be no smaller than 1.5 mm.

Figure 2:
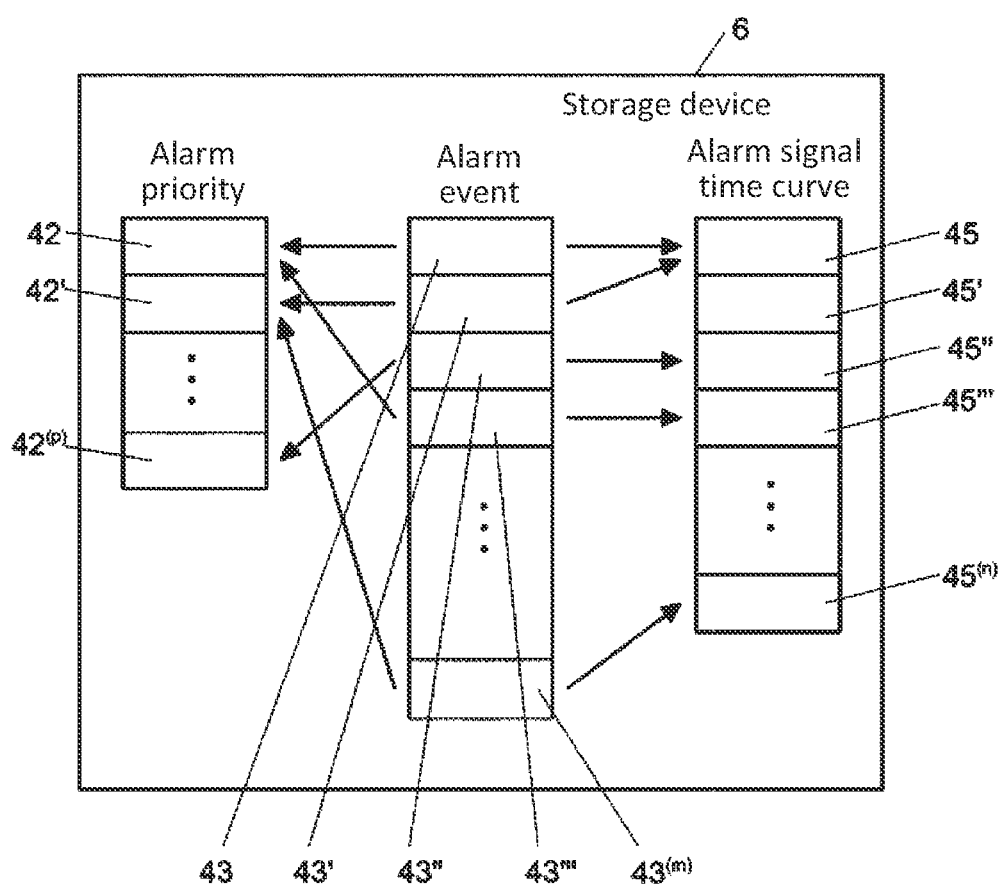
FIG. 2 is a schematic representation of the storage device with the assignment of defined alarm priorities and defined alarm signal time curves to defined alarm events.

FIG. 2 shows the storage device 6. Said storage device stores the assignment of the defined alarm events 43 to $43^{(m)}$ to the defined alarm priorities 42 to $42^{(p)}$ and the defined alarm signal time curves 45 to $45^{(n)}$ and the defined alarm signal time curves 45 to $45^{(n)}$. The storage device can be RAM assemblies (RAM: random access memory) or ROM modules (ROM: read-only memory). Other possible forms of implementation of the memory have already been listed above. The storage device is configured to store one or more defined alarm signal time curves and one or more alarm priorities such that each alarm signal time curve and each alarm priority is assigned to one or more defined alarm events. The assignment can be implemented, for example, via a table stored in the storage, in which an alarm event and the assigned alarm priority and a pointer to a storage area which contains the alarm signal time curve assigned to the alarm event are entered in each line.

Figure 3:
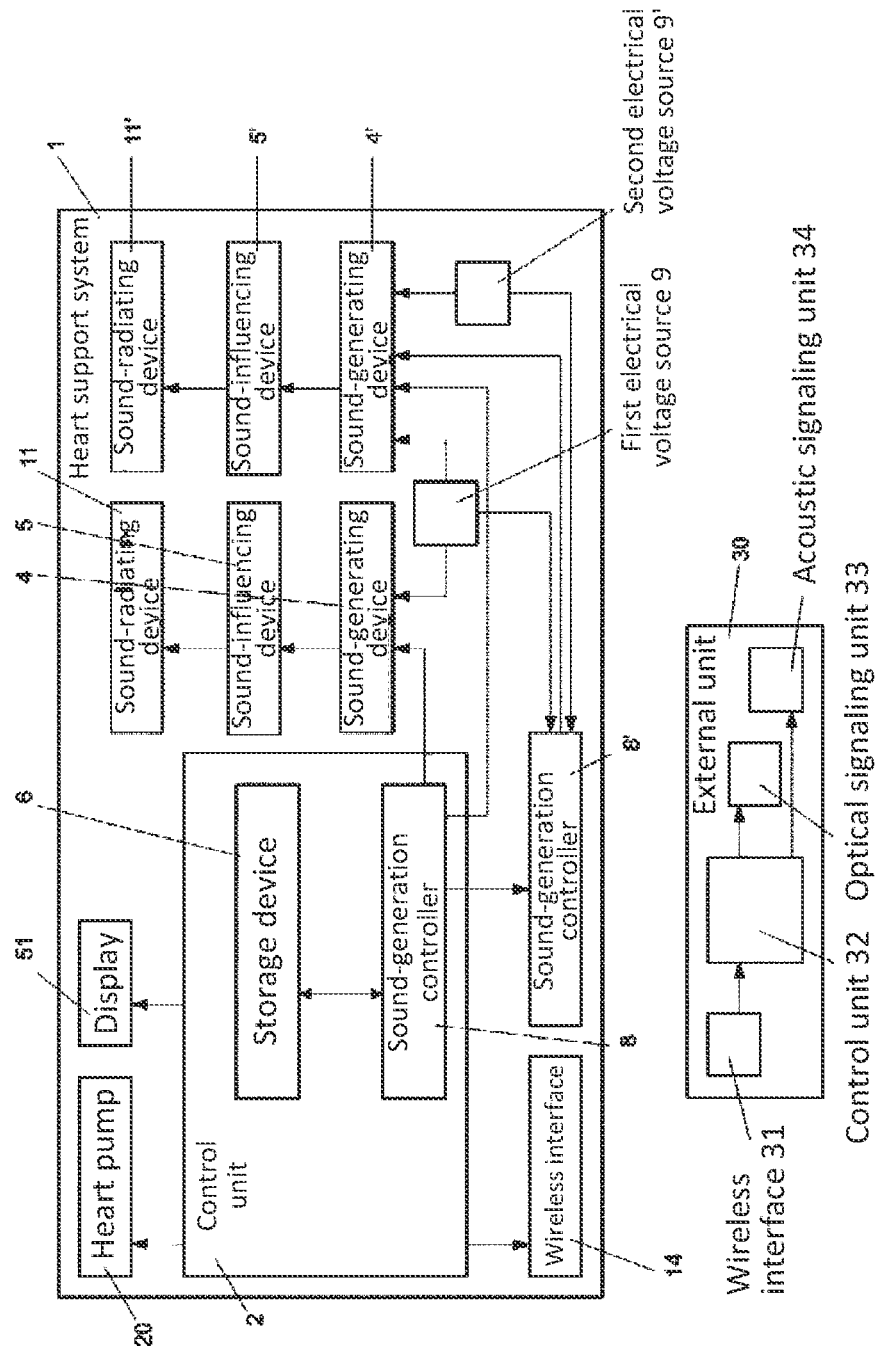
FIG. 3 illustrates a system overview of the basic alarm-relevant components of the claimed heart support system including optional components.

The basic components of the heart support system 1 are depicted in a system overview in FIG. 3. The central element is the control unit 2, the task of which is to detect and process events and in particular alarm events 43 and to process data and to carry out and coordinate control tasks in the heart support system 1. Said tasks include, among other things, the control of the heart pump 20, the control of the wireless interface 14 and the control of the sound-generation controller 8.

The first sound-generation controller 8 has the task of controlling the sound generation. For safety reasons, the heart support system 1 comprises a further, second sound-generation controller 8'. Said second sound-generation controller monitors the first sound-generation controller 8 and, if a functional failure of the first sound-generation controller 8 is detected, emits a warning signal with the aid of a second sound-generating device 4', a second sound-influencing device 5' and a second sound-radiating device 11'. One way of detecting the functional failure of the first sound-generation controller 8 is for the first sound-generation controller 8 to generate a pulsed voltage signal having a defined pattern at an electrical output during normal operation, which pulsed voltage signal is evaluated by the second sound-generation controller 8' at an electrical input. Said evaluation can be carried out, for example, by a simple microcontroller or else by an electronic circuit. The second sound-generation controller 8' can be configured such that said second sound-generation controller detects a deviation from the defined pattern, for example, the absence of a pulse, and then outputs a control signal that actuates the electrical control of a loudspeaker. The aforementioned electrical control of a loudspeaker can be implemented by an electronic oscillator circuit, with which a pulsed electrical voltage signal is generated which, as soon as said voltage signal is passed through to a loudspeaker, leads to the generation of a corresponding sound signal.

In addition, the heart support system 1 optionally comprises a display 51, optionally a wireless interface 14, and a first electrical voltage source 9 and optionally a second electrical voltage source 9'. The second electrical voltage source 9' is configured such that it can supply the second sound-generating device 4' and the second sound-generation controller 8' with electrical voltage if the first electrical voltage source 9 fails. The wireless interface 14 can be a WLAN interface, for example. Further forms of implementation for a wireless interface 14 have already been listed above.

The external unit 30 is configured to exchange data with the wireless interface 14 of the heart support system 1 via the wireless interface 31. The external unit 30 also comprises its own control unit 32, an optical signaling unit 33 and an acoustic signaling unit 34. The wireless interface 31 can be a WLAN interface, for example.

Figure 4:
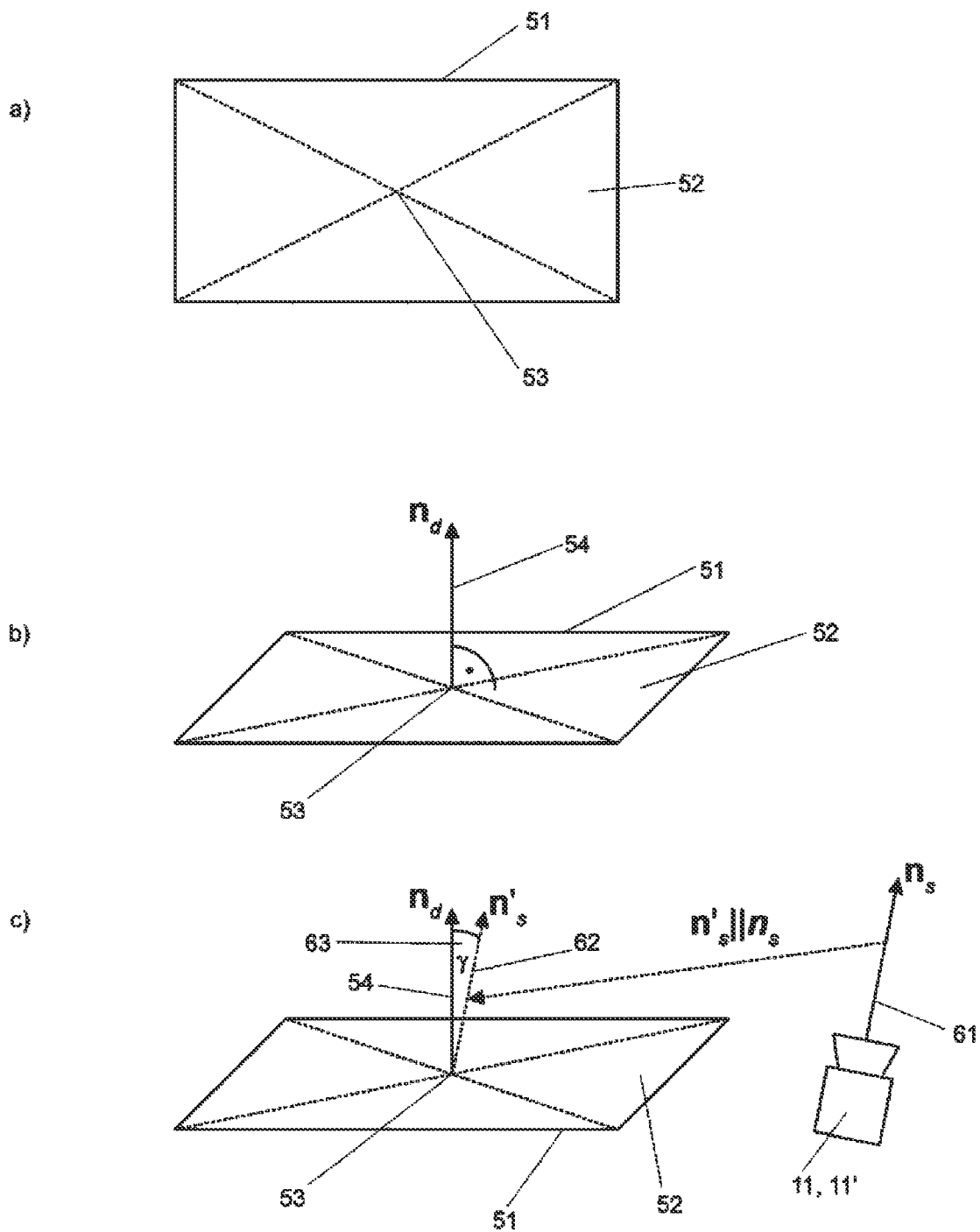
FIG. 4 is a schematic representation of the sound radiation.

FIG. 4 schematically shows the display 51 of the heart support system 1. A normal vector $n_d$ 54 is defined in the centroid 53 of the display surface 52, said normal vector being perpendicular to the display surface 52 and pointing away from the device. The sound is radiated by the sound-radiating device 11, 11', preferably such that the angle γ 63 between the normal vector $n_d$ 54 and the vector $n_s'$ 62, which runs parallel to the main sound radiation direction $n_s$ 61, is less than or equal to 90°.

Figure 5:
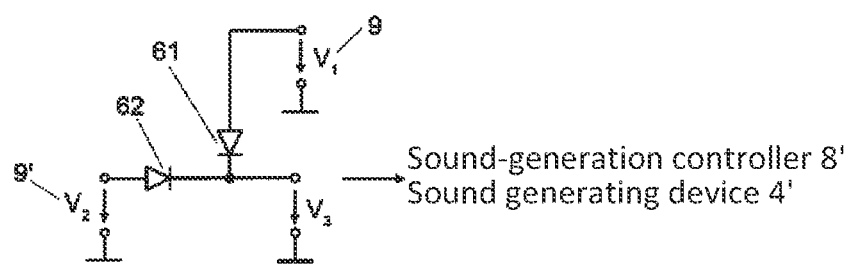
FIG. 5 is a schematic implementation variant for the interconnection of a first and a second voltage source.

FIG. 5 schematically shows a possibility of how two electrical voltage sources 9 and 9' can be connected to one another. The first electrical voltage source 9 provides an electrical voltage having the value V1. The second electrical voltage source 9' which serves as a backup voltage source provides an electrical voltage having the value V2. In this case, V1>V2, for example, V1=12V and V2=3V, both voltages V1 and V2 being measured against ground. The output voltage V3 of this circuit serves as an electrical voltage supply for the sound-generation controller 8', which actuates the sound-generating device 4'. In normal operation, that is, when the voltage values V1=12V and V2=3V are present, the diode 61 is open and the diode 62 is blocked, so that current can flow from the electrical voltage source 9 into the sound-generation controller 8' and the sound-generating device 4'; however, only a very small reverse current flows through the diode 62. However, if the electrical voltage source 9 breaks down, that is, V1=0V, diode 61 blocks and diode 62 opens. In this case, current flows from the electrical voltage source 9' into the sound-generation controller 8' and the sound-generating device 4'.

Figure 6:
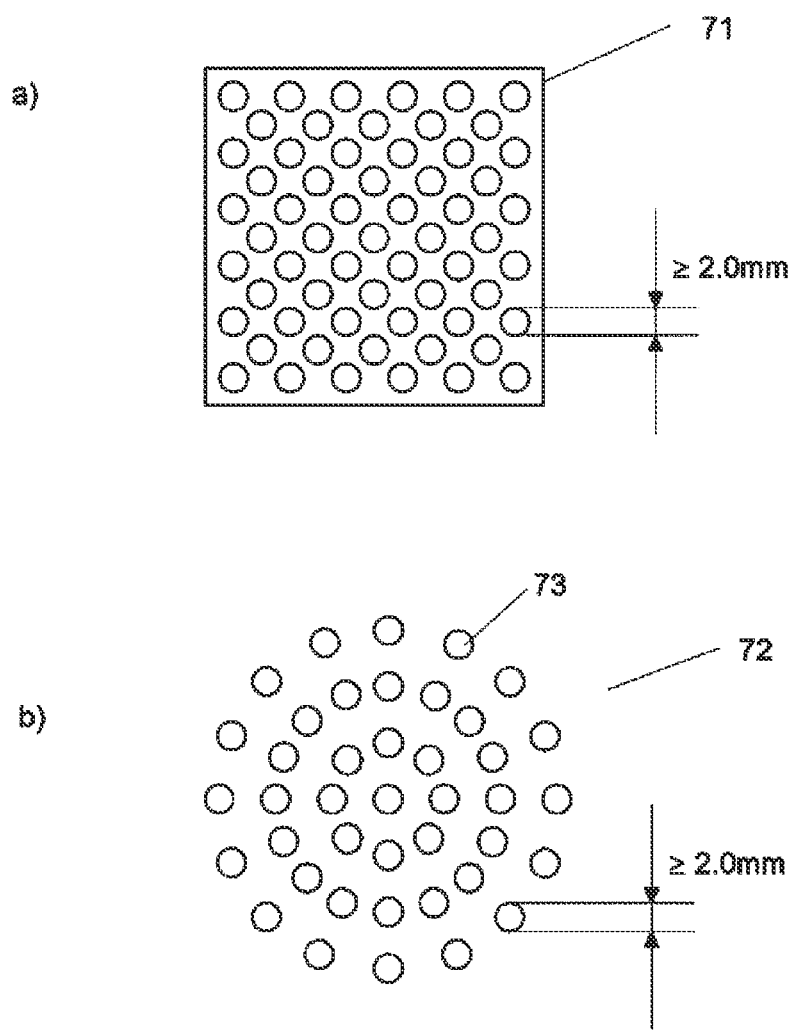
FIG. 6 illustrates implementation possibilities for sound-radiating devices.

FIG. 6 shows possible forms of implementation for the sound-radiating device 11, 11' with a rectangular field of perforations 71 and a circular field of perforations 72 having the openings 73 that are implemented, for example, by drilling holes in the housing of the heart support system 1. The opening diameters of the openings 73 in the field of perforations 71 or 72 preferably have values above 2 mm.

Figure 7:
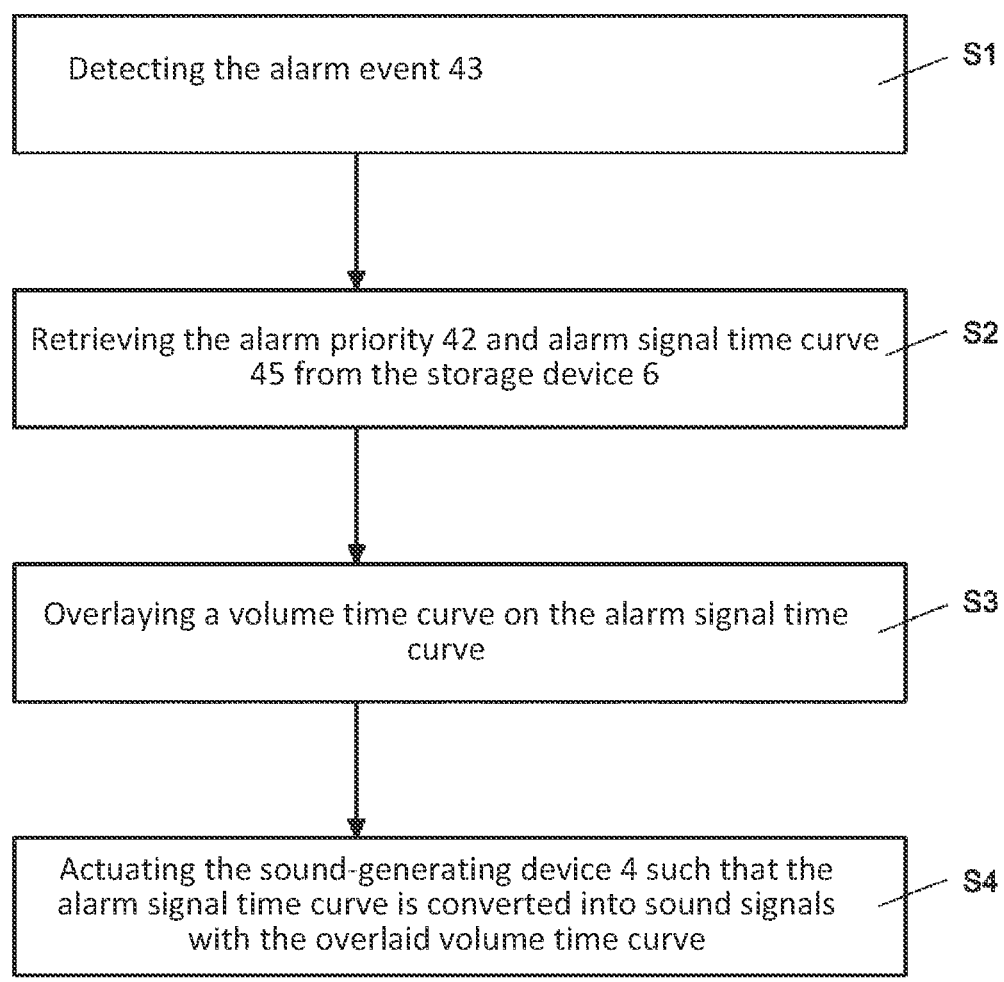
FIG. 7 illustrates the method steps for retrieving and modifying the alarm signal time curves.

FIG. 7 shows the method steps for retrieving and modifying the alarm signal time curves. As a first step S1, the claimed method for raising alarm has the detection of an alarm event in the heart support system. The detection can be implemented both by software and by hardware. In this case, for example, a voltage or current value present at the system inputs is compared with a reference value or, alternatively, a calculated value is compared with a reference value. The type of alarm event 43 is determined based on the type of comparison performed.

In a second method step S2, the alarm priority 42 assigned to the alarm event 43 and the assigned alarm signal time curve 45 are retrieved from a storage device 6.

In a third method step S3, a defined volume time curve is overlaid on the retrieved alarm signal time curve 45, based on the alarm priority 42 and on the length of time since the arrival of the alarm event 43. For example, the modification is such that the volume of the alarm signal time curve 45 is changed in a defined on-off pattern based on the alarm priority 42. On-off pattern means that the volume of the signal repeatedly changes from the value stored in storage to zero and vice versa in a defined manner. The time periods in which the volume value is zero are each referred to as the off phase, the other time periods as the on phase. In addition, the volume of the alarm signal is modified such that the volume during the on phases increases with increasing time measured from the detection of the alarm event up to a maximum value.

In a fourth method step S4, the sound-generating device 4 is actuated such that the alarm signal time curve is converted with the overlaid volume time curve into a sound signal.

The present disclosure includes, among other things, the following aspects:

1. A heart support system (1) with a first control unit (2) and at least one first sound-generating device (4), said control unit (2) being configured to detect and process events, and in particular alarm events (43), and to process data and carry out control tasks in the heart support system (1), characterized by
   at least one storage device (6), which is configured to store one or more defined alarm signal time curves (45) and one or more alarm priorities (42) such that each alarm signal time curve (45) and each alarm priority (42) is assigned to one or more defined alarm events (43),
   at least one sound-generation controller (8), which is configured such that when an alarm event (43) is detected, the controller overlays a volume time curve onto the alarm signal time curve (45) assigned to the alarm event (43) in the storage device (6), said volume time curve being based on the alarm priority (42) assigned to the respective alarm event (43) in the storage device (6) and the length of time since the detection of the alarm event (43),
   the aforementioned sound-generation controller device (8), which is configured to actuate one or more sound-generating devices (4) upon detecting an alarm event (43) such that the sound generating devices convert the aforementioned alarm signal time curve (45) with the defined overlaid volume time curve into sound signals.
2. The heart support system (1) according to aspect 1, wherein the heart support system (1) comprises a heart pump (20) and wherein the control unit (2) controls the heart pump (20).
3. The heart support system (1) according to aspect 1 or 2, characterized by at least one second, electrically operated sound-generating device (4') that can be actuated separately from the first.
4. The heart support system (1) according to aspect 3, characterized in that the sound-generating devices (4, 4') contain a broadband speaker and a narrowband speaker.
5. The heart support system (1) according to aspect 3, characterized in that the sound-generating devices (4, 4') contain two broadband loudspeakers.
6. The heart support system (1) according to any one of the preceding aspects, characterized by at least one second control unit (8'), which is configured to detect a functional failure of the first sound-generation controller unit (8) and to actuate at least one sound-generating device (4, 4') such that the sound-generating device (4, 4') generates defined sound signals.
7. The heart support system (1) according to any one of the preceding aspects, wherein the heart support system (1) contains a first electrical voltage source (9), characterized by a second electrical voltage source (9'), which is configured to, if the first electrical voltage source (9) fails, to supply at least one sound-generating device (4') and the second control unit (8') with voltage.
8. The heart support system (1) according to any one of the preceding aspects, characterized by at least one sound-radiating device (11), which is configured to influence the sound radiation.
9. The heart support system (1) according to aspect 8, wherein the heart support system contains a display (51), characterized in that the angle γ (63) between the main direction of the sound radiation (61) by the sound-radiating devices (11, 11') and the normal vector (63) of the display (51) pointing away from the display (51) has a value less than or equal to 90°.
10. The heart support system (1) according to any one of the preceding aspects, characterized by at least one sound-influencing device (5, 5'), which is configured to influence the weighting of the sound frequencies.
11. The heart support system (1) according to any one of the preceding aspects, characterized by a wireless interface (14), which is configured to exchange data with the wireless interface (31) of an external unit (30).
12. The heart support system (1) according to any one of the preceding aspects, characterized in that the external unit (30) comprises an optical signaling unit (33).
13. The heart support system (1) according to any one of the preceding aspects, characterized in that the external unit (30) comprises an acoustic signaling unit (34).
14. A method for the manner of raising alarm for a heart support system, characterized by
    detecting S1 an alarm event 43,
    retrieving S2 the alarm priority 42 assigned to the alarm event 43 and the alarm signal time curve 45 assigned to the alarm event 43 from the storage device 6,
    overlaying S3 a volume time curve on the alarm signal time curve 45 which is based on the alarm priority 42 and on the length of time since the alarm event 43 was detected,
    actuating S4 the sound-generating device 4, such that the alarm signal time curve 45 is converted with the overlaid volume time curve into a sound signal.

The invention claimed is:
1. A heart support system comprising:
a first control unit;
at least one first sound-generating device, said control unit configured to detect and process events including alarm events, and to process data and carry out control tasks in the heart support system;
   at least one storage device, which is configured to store one or more defined alarm signal time curves and one or more alarm priorities, such that each alarm signal time curve and each alarm priority assigned to one or more defined alarm events,
   at least one sound-generation controller, which is configured to, when an alarm event is detected, overlay a volume time curve onto the alarm signal time curve assigned to the alarm event in the storage device, said volume time curve based on the alarm priority assigned to the respective alarm event in the storage device and the length of time since the detection of the alarm event, wherein the at least one sound-generation controller is configured to actuate one or more sound-generating devices upon detection of an alarm event such that the sound generating devices convert the aforementioned alarm signal time curve with the defined overlaid volume time curve into sound signals, at least one second, electrically operated sound-generating device configured to be actuated separately from the first, at least one second control unit, which is configured to detect a functional failure of the first sound-generating controller and to actuate the second sound-generating device such that the second sound-generating device generates defined sound signals.

2. The heart support system of claim 1, wherein the heart support system comprises a heart pump and wherein the control unit controls the heart pump.

3. The heart support system of claim 1, characterized in that the sound-generating devices contain a broadband speaker and a narrowband speaker.

4. The heart support system of claim 1, characterized in that the sound-generating devices contain two broadband loudspeakers.

5. The heart support system of claim 1, wherein the heart support system contains a first electrical voltage source and comprises a second electrical voltage source, which is configured to, if the first electrical voltage source fails, to supply at least one sound-generating device and the second control unit with voltage.

6. The heart support system of claim 1 comprising at least one sound-radiating device, which is configured to influence the sound radiation.

7. The heart support system of claim 6, wherein the heart support system contains a display, characterized in that an angle y between a main direction of a sound radiation by the sound-radiating devices and a normal vector of the display pointing away from the display has a value less than or equal to 90°.

8. The heart support system of claim 1 comprising at least one sound-influencing device, which is configured to influence weighting of the sound frequencies.

9. The heart support system of claim 1 comprising a wireless interface, which is configured to exchange data with the wireless interface of an external unit.

10. The heart support system of claim 9, characterized in that the external unit comprises an optical signaling unit.

11. The heart support system of claim 9, characterized in that the external unit comprises an acoustic signaling unit.

12. A method for a manner of raising alarm for a heart support system comprising detecting an alarm event, retrieving an alarm priority assigned to the alarm event and an alarm signal time curve assigned to the alarm event from a storage device, overlaying a volume time curve on the alarm signal time curve which is based on the alarm priority and on a length of time since the alarm event was detected, actuating a sound-generating device, such that the alarm signal time curve is converted with the overlaid volume time curve into a sound signal.

\* \* \* \* \*